United States Patent [19]

Schnabel

[11] 3,987,075

[45] *Oct. 19, 1976

[54] SOLVENT EXTRACTION AND DISTILLATION TECHNIQUE FOR PURIFICATION OF ORGANIC ISOCYANATES

[75] Inventor: Wilhelm J. Schnabel, Branford, Conn.

[73] Assignee: Olin Corporation, New Haven, Conn.

[ * ] Notice: The portion of the term of this patent subsequent to June 11, 1991, has been disclaimed.

[22] Filed: June 5, 1974

[21] Appl. No.: 476,763

Related U.S. Application Data

[63] Continuation-in-part of Ser. No. 214,769, Jan. 3, 1972, Pat. No. 3,816,496.

[52] U.S. Cl. .............................. 260/453 SP; 203/43
[51] Int. Cl.² ..................................... C07C 119/042
[58] Field of Search .............................. 260/453 SP

[56] References Cited

UNITED STATES PATENTS 3,211,631   10/1965   Fuchs............................ 260/453 X
3,816,496   6/1974   Schnabel...................... 260/453 SP Primary Examiner—Lewis Gotts
Assistant Examiner—Dolph H. Torrence
Attorney, Agent, or Firm—Donald F. Clements; James B. Haglind; Thomas P. O'Day

[57] ABSTRACT

Alkyl substituted benzene is used as a solvent to extract organic isocyanates from crude reaction mixtures containing organic isocyanates. The crude reaction mixture is admixed with the alkyl substituted benzene solvent and heated to a temperature in the range from 130° C. to about 280° C. for a solvent extraction period ranging from about 0.5 to about 24 hours. The alkyl substituents on the benzene contain between 1 and 15 carbon atoms and sufficient substituents to provide at least two carbon atoms in the substituents.

17 Claims, 1 Drawing Figure

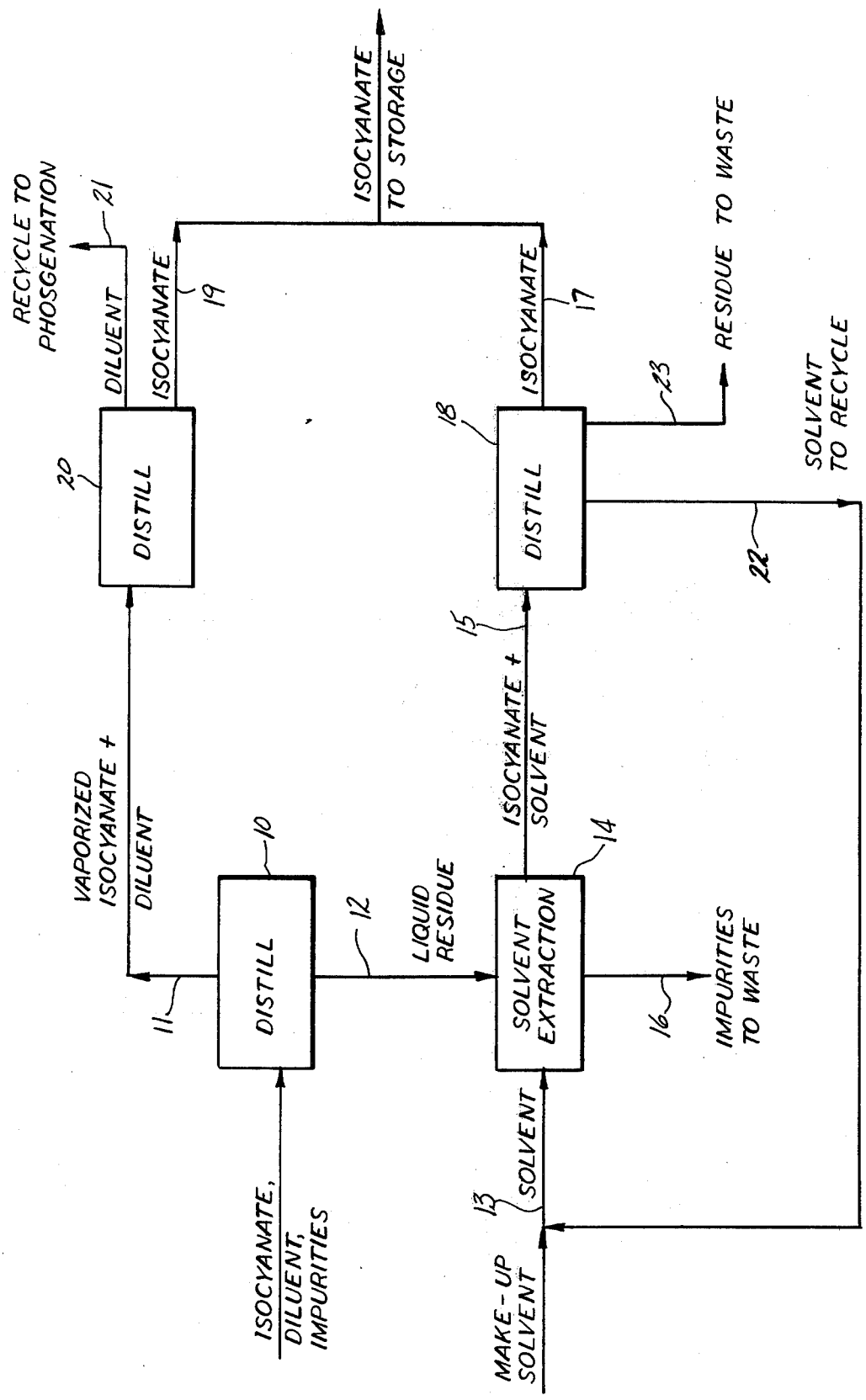

SOLVENT EXTRACTION AND DISTILLATION TECHNIQUE FOR PURIFICATION OF ORGANIC ISOCYANATES

This application is a continuation-in-part of my co-pending application, Ser. No. 214,769, filed Jan. 3, 1972, now U.S. Pat. No. 3,816,496.

This invention relates to an improved process for recovering organic isocyanates from crude mixtures containing the same.

Various processes have been developed for the preparation of organic isocyanates. In one process a primary amine or amine hydrochloride is reacted with phosgene to yield the desired isocyanate. In another process other compounds which liberate phosgene during the reaction are used as a substitute for phosgene. It is also known that potassium cyanate can be reacted with an organic sulfate to yield the corresponding organic isocyanate. It has also been proposed to produce organic isocyanates by pyrolyzing an N-substituted carbamate followed by separation of the corresponding isocyanate from the pyrolyzed product before the latter has had time to reunite and form the starting N-substituted carbamate. All of these reactions can be carried out in the presence or in the absence of an inert organic liquid diluent.

Elevated temperatures are generally employed to carry out the above-mentioned reactions and/or to effect distillation of the reaction products formed by them. These elevated temperatures cause the formation of undesirable by-products such as polymerized isocyanates which are extremely difficult to separate from the organic isocyanate product. Also ureas are formed as by-products during the phosgenation of amines as a result of a reaction between the formed isocyanates with unconverted amines. In the case of "crude" toluene diamine the ortho isomers present in the crude mixture forms essentially, especially under the conditions of large scale industrial production, cyclic ureas such as methyl benzimidazolones. Each mole of these ureas reacts with one or two moles of isocyanate to form biuretes, thus decreasing generally the yield of isocyanates. In many instances these by-products are highly viscous fluids or solids which tend to occlude or chemically combine with a substantial amount of the organic isocyanate product. As a result the yield of organic isocyanate recovered in these processes is usually substantially below the theoretical value.

A solvent extraction technique useful for recovering organic isocyanate values from crude organic isocyanate solutions is disclosed in U.S. Pat. No. 3,211,631, issued Oct. 12, 1965. Although this process gives improved yields of isocyanates, the utilization of aliphatic hydrocarbons such as pentane or hexane does not give a complete recovery of the chemically bound isocyanate because the boiling point of this type of solvent at atmospheric pressure is not high enough to achieve cleavage of the chemically bound isocyanates. There is a need for solvents which are capable of more effectively extracting both the unbound organic isocyanates as well as the chemically bound isocyanates present in crude organic isocyanates, while simultaneously inhibiting the extraction of undesired impurities.

It is the primary object of this invention to provide an improved process for producing organic isocyanates.

Another object of the invention is to provide an improved process for increasing the yield of organic isocyanates in processes for producing them.

A further object of the invention is to provide an improved liquid extraction and distillation technique for recovering organic isocyanates from impure solutions containing them.

Still another object of the invention is to provide an improved process for producing organic isocyanates in which the products of the reaction are easier to handle.

These and other objects of the invention will be apparent from the following detailed description thereof.

The above-mentioned objects, as well as those not specifically recited, are accomplished, for example, in one embodiment of the invention shown in the FIGURE.

In the process of this invention, a crude reaction mixture containing an organic isocyanate, an inert organic liquid diluent and impurities is first distilled 10 to vaporize 11 substantially all of the inert organic liquid diluent and a portion of the organic isocyanate, and to yield a liquid residue 12 containing substantially all of the impurities and the remainder of the organic isocyanate. Liquid residue 12 is admixed in a solvent extraction 14 with an inert liquid alkyl benzene solvent 13 for the organic isocyanate to yield a first liquid phase 15 comprised of the organic isocyanate dissolved in the inert liquid alkyl benzene solvent, and a second phase 16 comprised of the impurities. The first liquid phase 15 is separated from the impurities in second phase 16 by decantation, centrifuging, filtration or the like. Depending upon the alkyl benzene solvent, the organic isocyanate being recovered and the temperature conditions, second phase 16 may be in liquid form, slurry form or solid form, and appropriate separation means is used to separate the alkyl benzene solution of the organic isocyanate from the second phase containing impurities. First liquid phase 15 is distilled (18) or otherwise processed to separate the organic isocyanate 17 from the alkyl benzene solvent 22. If desired, an impurities bleed-off stream 23 may be employed in distillation 18 to remove a small amount of impurities that may build up in the distillation step which are sent to waste disposal.

Vaporized isocyanate and diluent 11 from distillation 10 is further distilled 20 to form organic isocyanate 19 and inert organic liquid diluent 21. Organic isocyanate 19 from distillation 20 is combined with organic isocyanate 17 separated from the inert liquid alkyl benzene solvent 22 in distillation 18 and conveyed to storage. Diluent 21 and solvent 22 may each be recovered and recycled. The yield of organic isocyanate obtained by this novel technique is substantially greater than the yield of organic isocyanate obtained by conventional distillation techniques.

In another embodiment organic isocyanates such as toluene diisocyanates are prepared by reacting toluene diamine with phosgene in the presence of a solvent such as monochlorobenzene, as described, for example, in U.S. Pat. No. 3,287,387, issued Nov. 22, 1966. In the process of U.S. Pat. No. 3,287,387, the crude reaction product is distilled to remove hydrogen chloride, monochlorobenzene, phosgene and a major portion of the toluene diisocyanate, leaving a crude toluene diisocyanate residue containing impurities. This crude residue may contain a substantial amount of toluene diisocyanate values, which is difficult to completely recover by distillation or other conventional techniques. The novel process of this invention, utilizing an alkyl benzene as a solvent extraction medium is capable of dissolving substantial amounts of the toluene diisocyanate values without dissolving significant amounts of undesirable impurities.

In more detail, the above-mentioned reactions, particularly the reaction of phosgene with a primary amine, are generally carried out in an inert liquid organic diluent. Typical examples of suitable diluents include benzene, toluene, xylene, dioxane, chlorinated hydrocarbons such as carbon tetrachloride, trichloroethylene, ethylene dichloride, chlorobenzenes such as 1,3-dichlorobenzene, ketones such as methyl ethyl ketone, etc., petroleum naphtha, etc., and mixtures thereof.

The resulting crude reaction product containing the inert organic liquid diluent, the organic isocyanate and dissolved impurities is subjected to one of several distillation techniques to separate substantially all of the inert organic liquid diluent and a portion, preferably a major portion, of the organic isocyanate product. Generally this separation is carried out by distilling the crude reaction product to first remove a fraction predominating in the inert organic liquid diluent, which is collected for recycling to the initial reaction. A second fraction is then separated by distillation which is comprised of a portion, preferably a major portion, of the organic isocyanate, which is collected. If desired, the crude reaction mixture can be distilled to yield a fraction containing both the inert organic liquid diluent and the organic isocyanate, and this fraction, after condensing or other treatment, can then be further processed to yield a concentrate of organic isocyanate and a concentrate of inert liquid diluent.

After separation of the inert organic liquid diluent and a portion of the organic isocyanate, an impurities residue is produced which contains a portion, preferably a minor portion, of the organic isocyanate and substantially all of the impurities. This impurities residue contains free organic isocyanate as well as chemically combined organic isocyanates as the by-products and polymers of the organic isocyanate produced. This impurities residue, if subjected to distillation or other processing technique which involves elevated temperatures, will solidify on cooling to room temperature to a brittle mass containing occluded or chemically combined organic isocyanate product. In accordance with this invention, the impurities residue, which is generally in liquid form but also may be a slurry, or powdered solid form is admixed with an inert liquid alkyl benzene solvent for the organic isocyanate and heated as described below, which causes the formation of two phases, i.e., a first liquid phase and a second phase. The first liquid phase contains a significant proportion of both free and cleaved organic isocyanate dissolved in the solvent. The second phase is a highly viscous liquid, slurry or solid predominating in the impurities and by-products of the reaction. The first liquid phase and second phase are separated by decantation, filtration or other suitable techniques for separating the two phases. The first liquid phase is then distilled to separate the organic isocyanate from the inert liquid alkyl benzene solvent. The organic isocyanate is combined with the organic isocyanate product obtained from the first distillation step and the combined organic isocyanate is collected for storage or use.

As indicated above, the residue containing organic isocyanate may be in liquid, slurry or solid form. If desired, it may be cooled to effect solidification of the residue and the resulting residue is comminuted to a finely divided solid particle form. The resulting solids are then admixed with the alkyl benzene solvent and processed as described above for the liquid residue treatment.

Any inert liquid alkyl benzene solvent can be employed that is capable of dissolving the organic isocyanate without reacting with the organic isocyanate and without dissolving a significant portion of the impurities and by-products of the reaction contained in the crude isocyanate solution. Typical examples of suitable inert liquid alkyl benzene solvents are those in which the alkyl moiety contains between 1 and 15 and preferably between about 1 and about 14 carbon atoms. More preferably, the alkyl benzene contains from about 6 to about 14 carbon atoms in the alkyl moiety. Either straight chain, branched chain or cyclic alkyl substituents may be employed, and each type is included in the terms "alkyl-substituted benzene" and "alkyl benzene" as used throughout the description and claims. The number of alkyl substituents on the benzene is between 1 and about 4. However, the total of carbon atoms in the alkyl substitutents should be at least two. Thus, if the alkyl substituent is methyl, there should be at least two methyl substituents on the benzene. Typical examples of suitable inert liquid alkyl benzene solvents include: trimethylbenzene, tetraline, diethylbenzene, dimethylbenzene, ethylbenzene, n-butyl benzene, isopropyl benzene, tertiarybutyl benzene, n-hexyl benzene, cyclohexyl benzene, decyl benzene, undecyl benzene, dodecyl benzene, tridecyl benzene, tetradecyl benzene, and the like, and mixtures thereof. Preferred alkylbenzene solvents include dodecyl benzene, cyclohexyl benzene, and mixtures of undecyl benzene, dodecyl benzene and tridecyl benzene, with or without decyl benzene and tetradecyl benzene being present.

Mixtures of alkyl benzenes that are particularly suitable for use as the solvent in the novel solvent extraction technique of this invention are mixtures of higher alkyl benzenes wherein the alkyl moiety contains the following distribution of carbon atoms:

| Alkyl | Percent by Weight |
|---|---|
| decyl ($C_{10}$) | 0 – 25 |
| undecyl ($C_{11}$) | 5 – 60 |
| dodecyl ($C_{12}$) | 30 – 50 |
| tridecyl ($C_{13}$) | 3 – 60 |
| tetradecyl ($C_{14}$) | 0 – 25 |

Typical mixtures of this type are sold commercially as Monsanto Linear Alkylates A-215, A-222, A-225, A-228 and A-230 having the following typical analyses.

Homolog Distribution (%)*:

| | Alkylate Number | | | | |
|---|---|---|---|---|---|
| | A-215 | A-222 | A-225 | A-228 | A-230 |
| $C_{10}$** | 7 | 3 | 4 | — | — |

-continued

Homolog Distribution (%)*:

| | Alkylate Number | | | | |
|---|---|---|---|---|---|
| | A-215 | A-222 | A-225 | A-228 | A-230 |
| $C_{11}$ | 56 | 37 | 42 | 9 | 4 |
| $C_{12}$ | 33 | 37 | 38 | 44 | 24 |
| $C_{13}$ | 4 | 21 | 15 | 41 | 49 |
| $C_{14}$ | — | 2 | 1 | 6 | 23 |
| 2-Phenyl Isomer (%)* | 12 | 15 | 14 | 17 | 21 |
| Average Molecular Weight | 237 | 244 | 242 | 253 | 259 |

*Percent by weight by gas-liquid chromatography
**Number of carbon atoms in alkyl moiety.

The proportion of inert liquid alkyl benzene solvent employed should be sufficient to dissolve substantially all of the organic isocyanate contained in the residue in occluded, chemically bound or other form. This proportion will depend upon the type of solvent employed, the type of organic isocyanate, and the degree of solubility of the organic isocyanate in the inert liquid alkyl benzene solvent. Generally the inert liquid alkyl benzene solvent proportion is between about 50 and about 3000 percent and preferably between about 100 and about 2000 percent by weight of the organic isocyanate.

The process of this invention can be utilized for the recovery of organic isocyanates generally; i.e., aliphatic cycloaliphatic, alkyl, aryl, aralkyl, heterocyclic and aryl mono-, di- and polyisocyanates. Examples of organic isocyanates which can be recovered according to the process of this invention are hexylisocyanate, octylisocyanate, dodecylisocyanate, octadecylisocyanate, tetramethylene diisocyanate, pentamethylene diisocyanate, octamethylene diisocyanate, undecamethylene diisocyanate, dodecamethylene diisocyanate, 3,3'-diisocyanato dipropyl ether, cyclohexyl isocyanate, tetrahydro-$\beta$-naphthyl isocyanate, tetrahydro-$\beta$-naphthyl isocyanate, xylene disocyanate, diphenylmethane 4,4'-diisocyanate, $\beta,\beta'$-diphenylpropane 4,4'-diisocyanate, benzyl isocyanate, phenylethylisocyanate, p-isocyanato benzyl isocyanate, phenyl isocyanate, p-cetyl phenyl isocyanate, p-dodecylphenyl isocyanate, 5-dodecyl-2-methylphenyl isocyanate, 3-nitro-4-dodecylphenyl isocyanate, p-cetyloxphenyl isocyanate, metaphenylene diisocyanate, p-phenylene diisocyanate, naphthylene-1,4-diisocyanate, 2,4-tolylene diisocyanate, 2,6-tolylene diisocyanate, 1,3,5-benzene triisocyanate, tetrahydrofurfuryl isocyanate, and mixtures thereof.

The solvent extraction technique of this invention, including admixing of the organic isocyanate residue with the alkyl benzene solvent to effect dissolution of the organic isocyanate, and separation of the solvent phase from the residue, is carried out at a temperature in the range from about 130° to about 280° C. and preferably from about 150° and about 250° C. Higher or lower temperatures may be employed, depending upon the organic isocyanate being recovered and upon the solvent employed. However, the temperature should be high enough to free occluded organic isocyanate and cleave chemically bound isocyanate products. In addition, the pressure and temperature are controlled to prevent vaporization of the impurities during the solvent extraction step while maintaining the organic isocyanate in a liquid or vapor state, as desired. Solvent extraction in accordance with the process of this invention is preferably carried out at atmospheric pressure, but elevated pressure or partial vacuum may be employed if desired.

Contact between the solvent and the organic isocyanate containing residue to effect admixing and dissolving is preferably made in an agitated vessel provided with external or internal means for controlling the temperature and pressure. Contact time or solvent extraction period during which time organic isocyanate is extracted from the residue generally is in the range from about 0.5 to about 24 hours, and preferably from about 1 to about 20 hours.

After contact between and admixing of the solvent and organic isocyanate-containing material under these conditions, the first liquid phase and second phase are separated by decanting or other separation technique and the resulting organic isocyanate-containing solvent of the first liquid phase is then distilled to remove the organic isocyanate components. The recovered alkyl benzene solvent is then recycled to the initial solvent extraction step.

Those skilled in the art will recognize that more than one solvent extraction stage can be employed, and either concurrent or counter-current techniques may be employed without departing from the spirit of this invention.

The above-mentioned isocyanates having halogen substituents may also be treated in accordance with the process of this invention. The term "organic isocyanate" used throughout the description and claims is intended to include organic isocyanates with or without halogen substituents.

The following examples are presented to define the invention more fully without any intention of being limited thereby. All parts and percentages are by weight unless otherwise specified.

EXAMPLES 1–3

A crude solution of toluene diisocyanate was prepared by reacting toluene diamine with phosgene in a solvent of monochlorobenzene. Hydrogenchloride, unreacted phosgene and monochlorobenzene were stripped from the toluene diisocyanate-containing solution. The resulting toluene diisocyanate solution containing impurities is processed to remove most of the toluene diisocyanate, and the resulting residue is further evaporated in a wiping-film evaporator to remove another fraction of toluene diisocyanate in the overhead. The residue from the wiping-film evaporator contained about 30 percent diisocyanate and about 70 percent by-products. Analysis of the by-product component of the residue was as follows:

| | |
|---|---|
| Methyl benzimidazolones | 23 % |
| Isocyanurates (by IR) | 29 % |

-continued

| | |
|---|---|
| Carbodiimides (by IR) | 11 % |
| Ureas and/or biuretes (by difference) | 37 % |

The residue was cooled to solidification and the resulting solid was pulverized in a powder mill.

In each example about 100 grams of powdered residue was placed in a glass flask equipped with a thermometer, paddle stirrer, reflux condenser and sufficient dry solvent in the amount and type listed below in the Table. The resulting mixture was blanketed with nitrogen and gradually heated with an external oil bath with stirring. Presented below in the Table is the temperature and time of stirring. After cooling to room temperature and allowing to stand overnight, the undissolved portion was separated by filtration and dried in vacuo. Toluene diisocyanate content of the filtrate was determined by vapor phase chromatography and is recorded below in the Table.

EXAMPLES 4–5

The procedure of Examples 1–3 were repeated except that the wiping film residue contained about 20 percent by weight of toluene diisocyanate, as determined by vacuum distillation at 180° C and 0.5 mm., the balance of the residue being comprised of the same by-products as in Examples 1–3. In Example 4, the alkyl benzene was cyclohexyl benzene and in Example 5, the alkyl benzene was an alkyl benzene sold commercially as Monsanto Linear Alkylate A-215 having the following typical analysis:

| Homolog | Percent by Weight |
|---|---|
| decyl benzene | 7 |
| undecyl benzene | 56 |
| dodecyl benzene | 33 |
| tridecyl benzene | 4 |
| *2-phenyl isomer | 12 |
| Average Molecular Weight | 237 |

*As determined by gas-liquid chromotography produced by phosgenation of amines in the presence of an inert liquid diluent followed by distillation of substantially all of the inert diluent and a portion of the organic isocyanate, then admixing said crude reaction mixture with an inert liquid solvent for said organic isocyanate to form a first liquid phase containing said organic isocyanate and a second phase containing said impurities, and separating said first liquid phase from said second phase, the improvement which comprises employing as said inert liquid solvent an alkyl substituted benzene, wherein said alkyl contains between 6 and about 14 carbon atoms, and wherein said admixing is carried out at a temperature in the range of from about 130° to about 280° C.

2. The process of claim 1 wherein said crude reaction mixture is admixed with said alkyl substituted benzene for a solvent extraction period ranging from about 0.5 to about 24 hours.

3. The process of claim 2 wherein the proportion of said alkyl substituted benzene is between about 50 and about 3000 percent by weight of said organic isocyanate.

4. The process of claim 3 wherein the proportion of said alkyl substituted benzene is in the range from about 100 to about 2000 percent by weight of said organic isocyanate.

5. The process of claim 4 wherein said organic isocyanate is toluene diisocyanate.

6. In a process for extracting organic isocyanate from a crude reaction mixture containing organic isocyanate produced by phosgenation of amines in the presence of an inert liquid diluent followed by distillation of substantially all of the inert diluent and a portion of the organic isocyanate, then admixing said crude reaction mixture with an inert liquid solvent for said organic isocyanate to form a first liquid phase containing said organic isocyanate and a second phase containing said impurities, and separating said first liquid phase from said second phase, the improvement which comprises employing as said inert liquid solvent an alkyl substituted benzene selected from the group consisting of cyclohexyl benzene, decyl benzene, undecyl benzene, dodecyl benzene, tridecyl benzene, tetradecyl benzene and mixtures thereof, and wherein said admixing is

TABLE

SOLVENT EXTRACTION OF TOLUENE DIISOCYANATE WIPING-FILM EVAPORATOR RESIDUE

| | Solvent | | | | | Toluene Diisocyanate | |
|---|---|---|---|---|---|---|---|
| Example | Type | Boiling Point ° C. | Ml. Per 100 Grams Pulverized Residue | Temperature | Extraction Time Hours | Grams Extracted per 100 grams Pulverized Material | % Available TDI Recovery |
| 1 | Trimethyl-benzene | 169 | 300 | Stirred at Reflux | 7 | 17.0 | 56.5 |
| 2 | Tetraline | 206–207 | 300 | Stirred at 180° C | 5 | 23.6 | 78.5 |
| 3 | Diethyl-benzene | 175–181 | 500 | Stirred at Reflux | 7 | 28.4 | 94.6 |
| 4 | Cyclohexyl-benzene | 239° C at 740 mm. | 600 | Stirred at 180° C | 3 | 23.0 | 100 |
| 5 | Alkyl-benzene (C10–C13) | 79–80° C at 0.07 mm. | 600 | Stirred at 180° C | 2 | 17.6 | 88 |

Various modifications of the invention, some of which have been referred to above, may be employed without departing from the spirit of the invention.

What is desired to be secured by Letters Patent is:

1. In a process for extracting organic isocyanate from a crude reaction mixture containing organic isocyanate carried out at a temperature in the range of from about 130° to about 280° C.

7. The process of claim 6 wherein said alkyl substituted benzene is cyclohexyl benzene.

8. The process of claim 6 wherein said alkyl substituted benzene is decyl benzene.

9. The process of claim 6 wherein said alkyl substituted benzene is undecyl benzene.

10. The process of claim 6 wherein said alkyl substituted benzene is dodecyl benzene.

11. The process of claim 6 wherein said alkyl substituted benzene in tridecyl benzene.

12. The process of claim 6 wherein said alkyl substituted benzene is tetradecyl benzene.

13. The process of claim 6 wherein said alkyl substituted benzene is a mixture containing:
   a. from about 0 to about 25 percent by weight of decyl benzene,
   b. from about 5 to about 60 percent by weight of undecyl benzene,
   c. from about 30 to about 50 percent by weight of dodecyl benzene,
   d. from about 3 to about 60 percent by weight of tridecyl benzene, and,
   e. from about 0 to about 25 percent by weight of tetradecyl benzene.

14. The process of claim 13 wherein said solvent extraction period is in the range from about 1 to about 20 hours.

15. The process of claim 14 wherein said organic isocyanate is toluene diisocyanate.

16. The process of claim 15 wherein said temperature is in the range from about 150° C to about 250° C.

17. The process of claim 6 wherein said organic isocyanate is toluene diisocyanate.

* * * * *